United States Patent [19]

Buttermore

[11] Patent Number: 5,716,320
[45] Date of Patent: Feb. 10, 1998

[54] ILLUMINATED INTRAOCULAR SURGICAL INSTRUMENT

[76] Inventor: William J. Buttermore, 14240 Reelfoot Lake Dr., Chesterfield, Mo. 63017

[21] Appl. No.: 581,348

[22] Filed: Dec. 29, 1995

Related U.S. Application Data

[63] Continuation-in-part of Ser. No. 332,342, Oct. 31, 1994, abandoned.

[51] Int. Cl.⁶ ........................................ A61B 1/06
[52] U.S. Cl. ........................................ 600/104; 606/46
[58] Field of Search ........................... 600/104, 106, 600/130; 606/7, 127, 161, 166, 46, 4, 6; 607/116

[56] References Cited

U.S. PATENT DOCUMENTS

| | | | |
|---|---|---|---|
| 2,129,391 | 9/1938 | Wappler | 128/6 |
| 2,227,727 | 1/1941 | Leggiadro | 128/328 |
| 3,941,121 | 3/1976 | Olinger et al. | 128/6 |
| 4,300,564 | 11/1981 | Furihata | 600/104 |
| 4,379,462 | 4/1983 | Borkan et al. | |
| 4,459,989 | 7/1984 | Borkan | |
| 4,576,147 | 3/1986 | Hashiguchi | 128/6 |
| 4,584,988 | 4/1986 | Nishioka et al. | 128/6 |
| 4,607,622 | 8/1986 | Fritch et al. | 128/6 |
| 4,612,934 | 9/1986 | Borkan | |
| 4,617,013 | 10/1986 | Betz | 604/39 |
| 4,737,142 | 4/1988 | Heckele | 604/95 |
| 4,744,371 | 5/1988 | Harris | |
| 4,747,833 | 5/1988 | Kousai et al. | 604/161 X |
| 4,756,303 | 7/1988 | Kawashima et al. | 128/6 |
| 4,759,348 | 7/1988 | Cawood | 600/104 |
| 4,759,349 | 7/1988 | Betz et al. | 128/6 |
| 4,768,858 | 9/1988 | Hussein | 606/14 X |
| 4,782,819 | 11/1988 | Adair | 606/15 X |
| 4,793,353 | 12/1988 | Borkan | |
| 4,800,870 | 1/1989 | Reid, Jr. | 128/6 |
| 4,857,047 | 8/1989 | Amoils | 604/30 |

(List continued on next page.)

OTHER PUBLICATIONS

"Spinal Cord Stimulation For Chronic, Intractable Pain: Experience Over Two Decades" Neurosurgery, vol. 32, No. 3, Mar. 1993.

"Spinal Cord Stimulation For Chronic Pain" Neurosurgery Clinics Of North America, vol. 6, No. 1, Jan. 1995.

"Spinal Cord Stimulation For Chronic, Intractable Pain: Superiority Of Multi-Channel Devices" Pain, 44(1991), 119–130.

"The Role Of Spinal Cord Stimulation In Contemporary Of Pain Management", APS Journal 2(2): 91–99, 1993.

"Patient-Interactive, Computer-Controlled Neurological Stimulation System: Clinical Efficacy In Spinal Cord Stimulator Adjustment", Neurosurg., vol. 76, Jun. 1992.

(List continued on next page.)

Primary Examiner—William E. Kamm
Attorney, Agent, or Firm—Senniger, Powers, Leavitt & Roedel

[57] ABSTRACT

An illuminated intraocular surgical instrument having a grip and a tubular member supported by the grip and extending outwardly from its first end. A surgical tool has a shaft extending from within the tubular member outwardly from the distal end of the member to a free end. The shaft of the tool extends generally along the longitudinal axis of the tubular member as it exits the member through its open distal end. A plurality of light conducting fibers extending through the tubular member have terminal ends located generally at the distal end of the member. The light fibers are arranged at the open distal end of the tubular member generally around the shaft of the tool within the tubular member to illuminate the portion of the surgical tool disposed outwardly of the distal end of the tubular member and the area of operation, and to inhibit the casting of shadows by the surgical tool in the area of operation.

22 Claims, 3 Drawing Sheets

U.S. PATENT DOCUMENTS

| | | | |
|---|---|---|---|
| 4,862,874 | 9/1989 | Kellner | 128/6 |
| 4,872,837 | 10/1989 | Issalene et al. | 433/29 |
| 4,878,487 | 11/1989 | Sinnett | 128/20 |
| 4,921,326 | 5/1990 | Wild et al. | 128/6 X |
| 4,945,895 | 8/1990 | Takai et al. | 128/6 |
| 5,019,040 | 5/1991 | Itaoka et al. | 606/15 X |
| 5,083,549 | 1/1992 | Cho et al. | 600/108 |
| 5,119,832 | 6/1992 | Xavier . | |
| 5,121,754 | 6/1992 | Mullett . | |
| 5,201,730 | 4/1993 | Easley et al. | 606/4 |
| 5,217,456 | 6/1993 | Narcisco, Jr. | 606/15 X |
| 5,251,634 | 10/1993 | Weinberg | 128/642 |
| 5,254,121 | 10/1993 | Manevitz et al. | 595/50 X |
| 5,290,279 | 3/1994 | Bonati et al. | 606/15 |
| 5,328,365 | 7/1994 | Jacoby | 128/6 X |
| 5,335,648 | 8/1994 | Kozawa et al. | 128/6 |
| 5,370,672 | 12/1994 | Fowler et al. | 607/58 |
| 5,374,285 | 12/1994 | Vaiani et al. | 607/117 |
| 5,417,719 | 5/1995 | Hull et al. | 607/46 |
| 5,423,877 | 6/1995 | Mackey | 607/117 |
| 5,425,364 | 6/1995 | Ihran | 128/642 |
| 5,426,254 | 6/1995 | Pietroski et al. | 128/642 |
| 5,443,486 | 8/1995 | Hrdlicka et al. | 607/59 |
| 5,458,631 | 10/1995 | Xavier | 607/117 |
| 5,462,545 | 10/1995 | Wang et al. | 606/41 |

OTHER PUBLICATIONS

"Spinal Cord Stimulation For Chronic, Intractable Pain", Richard B. North, Electrical And Magnetic Stimulation Of The Brain And Spinal Cord, Copyright 1993, Chapter 25, pp. 289–301.

"Computer–Controlled Spinal Cord Stimulation Shown Superior To Conventional Programming", Anesthesiology News, Jun. 1996.

Site Microsurgical Systems, Incorporated, "Systems Descriptions, Accessories and Price List," Dec. 1981, pp. 12 and 15.

Kirwan Cauterizing Tool, shown in two photographs.

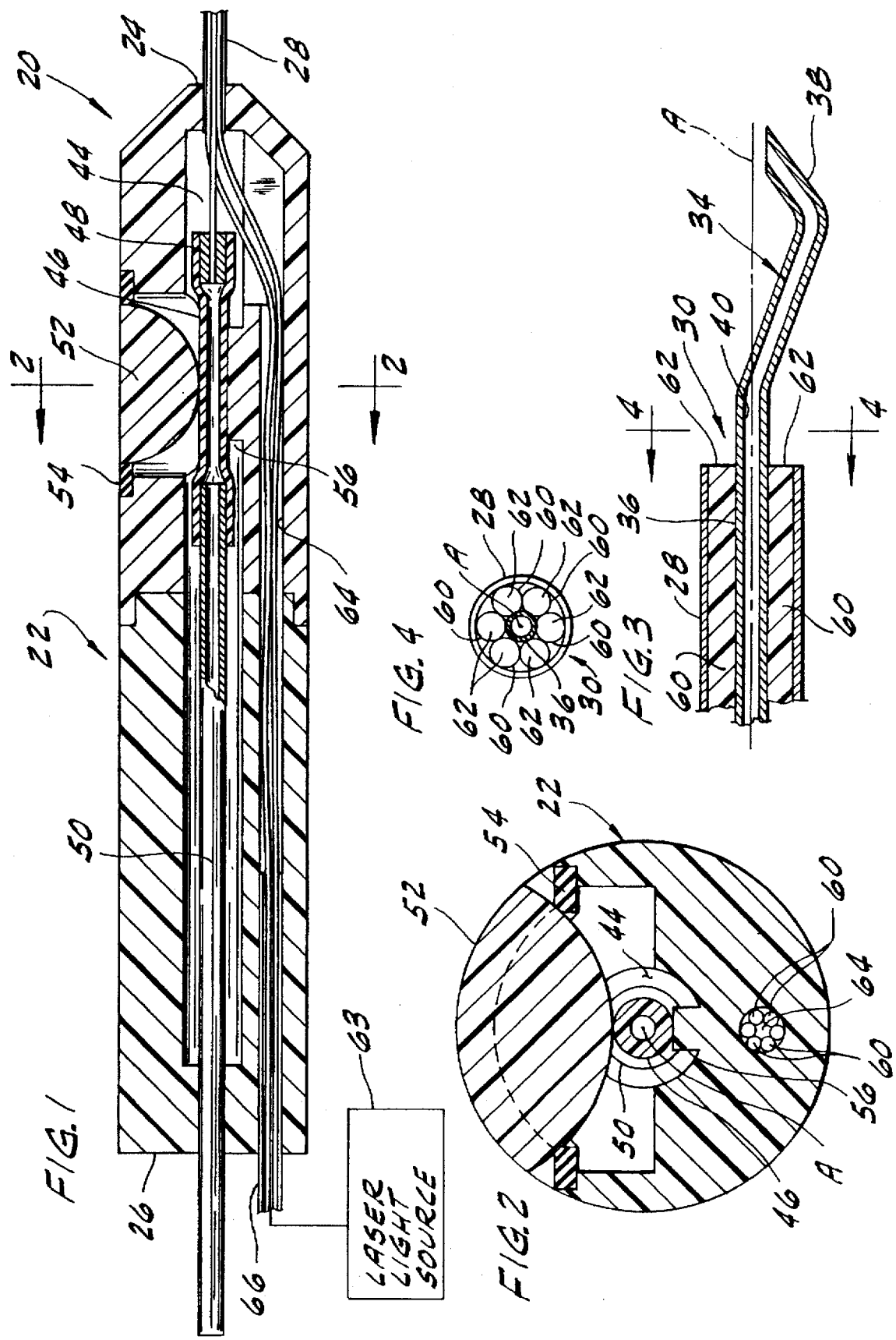

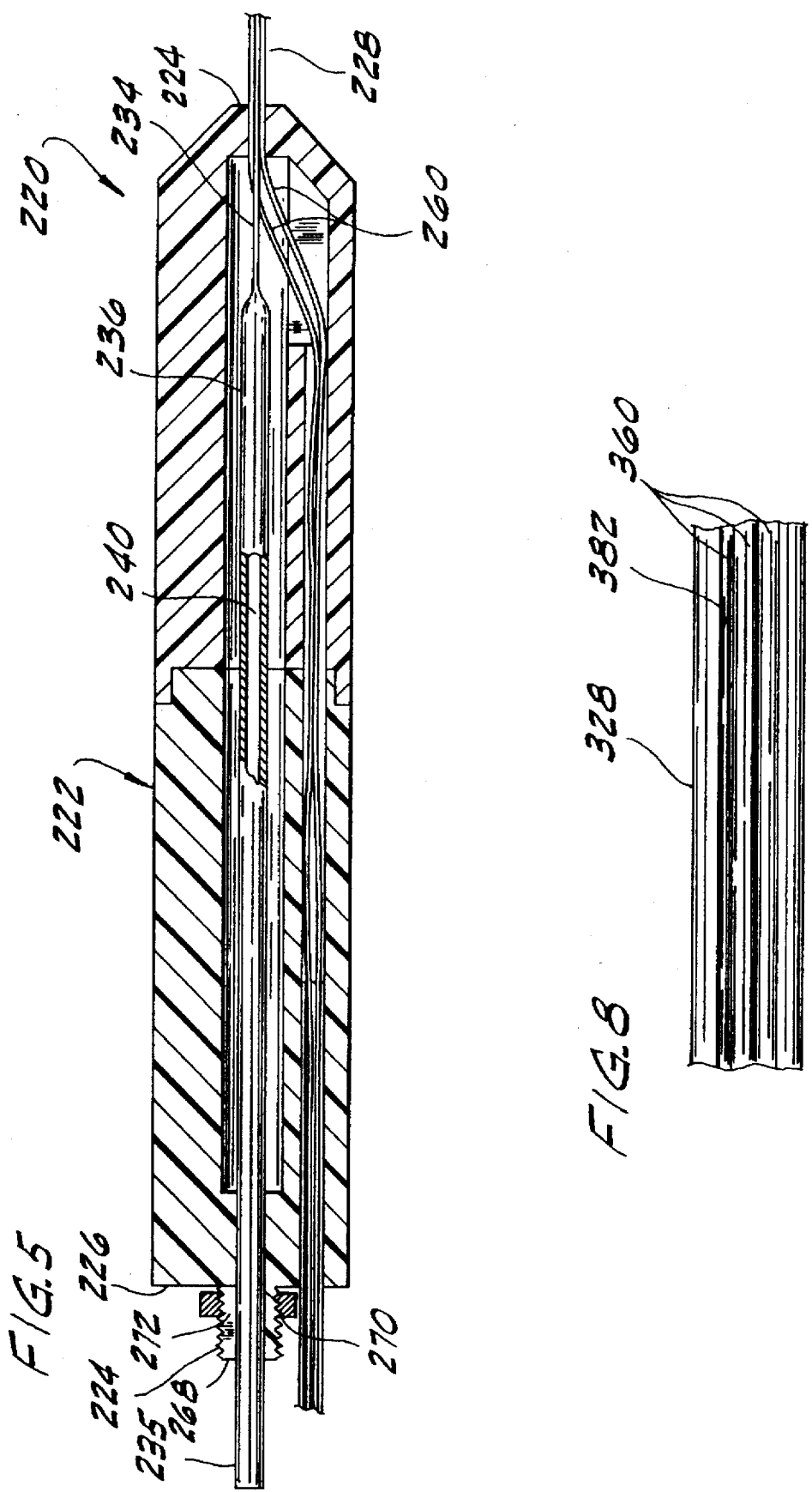

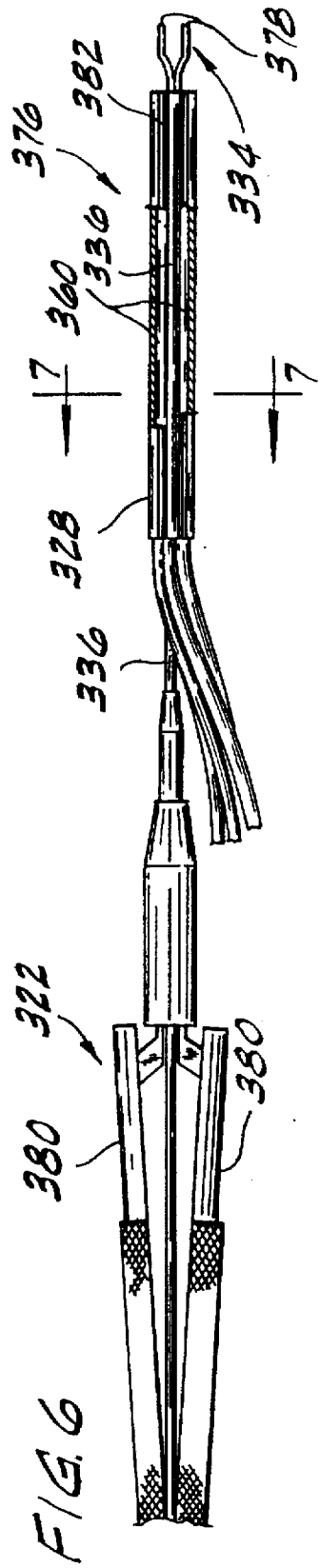
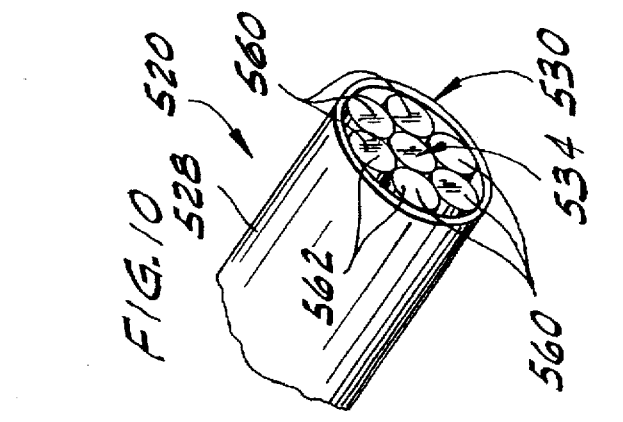
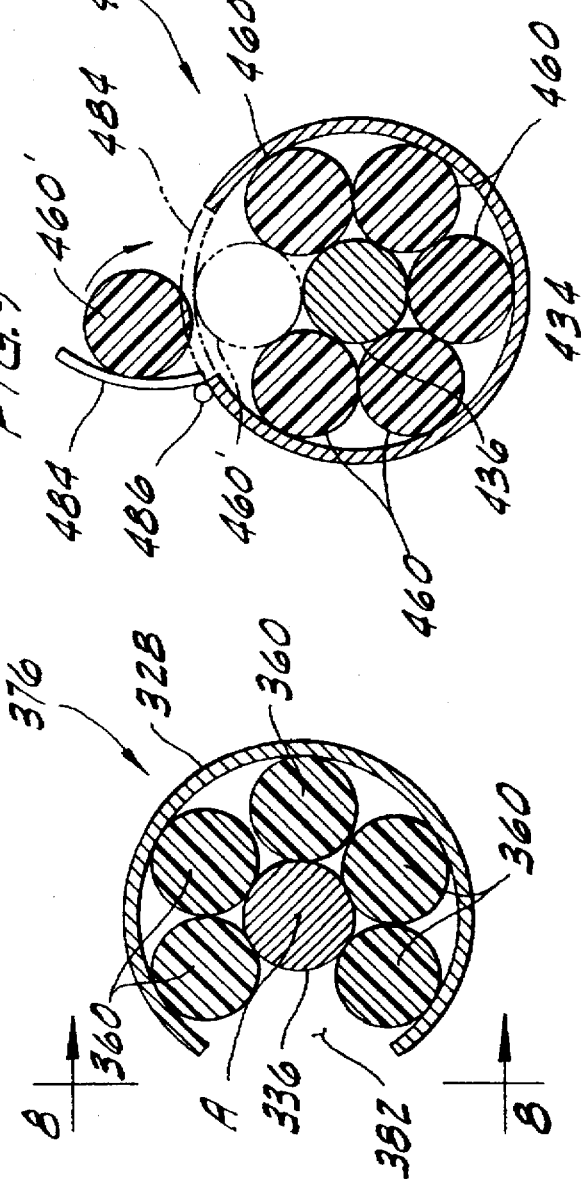

5,716,320

ILLUMINATED INTRAOCULAR SURGICAL INSTRUMENT

This application is a continuation-in-part of application Ser. No. 08/332,342, filed Oct. 31, 1994, now abandoned.

BACKGROUND OF THE INVENTION

This invention relates generally to surgical instruments and more particularly to illuminated surgical instruments employed in intraocular surgery.

Surgery which is conducted by the insertion of instruments through relatively small incisions in the body requires that a source of light also be inserted into the body. It is desirable to have the light source (e.g., light conducting fibers) associated with a surgical instrument which will be used to perform part of the operation, because this limits the number of incisions that have to be made. The small size of the operating space, particularly in eye surgery, makes it very desirable to limit the number of separate instruments used at the same time in the operating space. Moreover, it is also desirable to limit the number of different instruments which the surgeon must manipulate at the same time. Thus, the more functions a single surgical instrument can perform, the better, so long as the size of the instrument remains small. In addition, when the light source is associated with the tool, it is easier to aim the light where needed. However, mounting the light source on the tool can result in the tool casting shadows into the area of operation, obscuring the area. If the tool is moved off to the side of the light source, then less light is cast on the operating end of the tool and shadows remain a problem.

Surgical tools which are reused, must be of a very robust construction to withstand the rigors of autoclaving after each use. The special construction and materials necessary greatly adds to the cost of the instrument.

Presently, surgical instruments which carry their own light source are specially formed with structure permanently attached to the instrument for mounting the light carrying fibers. Thus, the cost of the instrument is increased.

SUMMARY OF THE INVENTION

Among the several objects of this invention may be noted the provision of an illuminated surgical instrument for insertion into a living body for surgical operation; the provision of such an instrument capable of performing multiple surgical functions; the provision of such an instrument in which illuminates while inhibiting the casting of shadows; the provision of such a surgical instrument in which the light fibers also function as electrical insulators; the provision of such an illuminated surgical instrument which is inexpensively made so that it is practical to dispose of it after one use.

In another aspect of the present invention, an illuminating device which is capable of releasable snap on attachment to surgical tools; the provision of such an illuminatin device which may be sterilized and reused on the same or other surgical tools; the provision of such an illuminating device which may be made inexpensively and disposed of after one use; the provision of such an illuminating device which is capable of illuminatin 9 the operating end of the surgical tool and adjacent area of operation while inhibiting the casting of shadows by the surgical tool.

Generally, an illuminated intraocular surgical instrument constructed according to the principles of the present invention comprises a rip having first and second ends and a tubular member supported by the grip. The tubular member has a central longitudinal axis and an open distal end spaced away from the first end of the grip. The tubular member is sized for insertion through the outer envelope of a living body for surgical operation within the body. A surgical tool has a shaft extending from within the tubular member outwardly from the distal end of the member. The tool has a free end spaced outwardly from the distal end of the tubular member. A plurality of light conducting fibers extending through the tubular member and having terminal ends located generally at the distal end of the member, are capable of emitting light. The shaft of the tool extends generally along the longitudinal axis of the tubular member as it exits the tubular member through its open distal end. The light fibers are arranged at the open distal end of the member generally around the shaft of the tool within the tubular member thereby to illuminate the portion of the surgical tool disposed outwardly of the distal end of the member and the area of operation, and to inhibit the casting of shadows by the surgical tool in the area of operation.

Generally, an illuminating device for a surgical instrument comprises a tubular member, substantially as described above. However, the tubular member has a longitudinal slit through which a portion of the surgical tool may pass for releasably mounting the illuminating device on the tool.

Other objects and features will be in part apparent and in part pointed out hereinafter.

BRIEF DESCRIPTION OF THE DRAWINGS

FIG. 1 is a longitudinal section of an illuminated surgical instrument;

FIG. 2 is an enlarged cross-section taken in the plane including lines 2—2 of FIG. 1.

FIG. 3 is an enlarged, fragmentary, sectional view of a surgical tool of the surgical instrument of FIG. 1.

FIG. 4 is a cross-section taken in the plane including lines 4—4 of FIG. 3.

FIG. 5 is a longitudinal section of a second embodiment of the surgical instrument;

FIG. 6 is an elevation of an illuminating device, constituting a third embodiment of the present invention, attached to a surgical tool;

FIG. 7 is a cross-section of a tubular member of a the illuminating device taken in the plane including line 7—7 of FIG. 6;

FIG. 8 is an enlarged, fragmentary top plan view of the tubular member taken from the vantage indicated by line 8—8 of FIG. 7;

FIG. 9 is a cross section of an illuminating device of a fourth embodiment of the present invention;

FIG. 10 is a fragmentary perspective of the distal end of a tubular member of a cauterizing surgical instrument of a fifth embodiment of the present invention.

Corresponding reference characters indicate corresponding parts throughout the several views of the drawings.

DETAILED DESCRIPTION OF THE DRAWINGS

Referring now to the drawings, and in particular to FIGS. 1-4, there is generally indicated at 20 an illuminated surgical instrument of this invention particularly adapted for use in minimally invasive surgery (e.g., eye surgery). The instrument 20 comprises a grip (designated generally by reference numeral 22) preferably sized so that a surgeon may hold it in one hand, the grip having a first end 24 and a second end 26. A tubular member 28 extending outwardly from the first end 24 of the grip 22 is secured generally at its inner end in an opening in the first end of the grip. In the preferred embodiments, the tubular member 28 is made from stainless steel and the grip 22 is preferably made of a suitable plastic material. The tubular member 28 has an open distal end (designated generally at 30) opposite the inner end enclosed within the grip 22. The outer diameter of the tubular member 28 is sized for insertion through a small incision in the outer envelope of a living body (not shown) for surgical operation within the body, and the inner diameter of the member is sized to receive a surgical tool, generally indicated at 34 (FIG. 3).

The surgical tool 34, preferably formed from stainless steel, has a shaft 36 extending through the tubular member 28 and outwardly from the open distal end 30 of the tubular member to a free end 38 spaced outwardly from the distal end of the tubular member. In the embodiment shown in FIG. 3, the free end 38 of the surgical tool 34 is formed as a pick for manipulating tissue within the body. Surgical tools formed for "manipulating" tissue, as used herein, include, without limitation, those tools formed for lifting, grasping, positioning and dissecting tissue. The shaft 36 of the tool extends generally along a central longitudinal axis A of the tubular member 28 as it exits the tubular member through its open distal end 30.

The surgical tool 34 is preferably formed with a longitudinal passage 40 opening at the free end 38 of the tool permitting fluid (liquid or gas) to pass through the tool for irrigation or aspiration of the area being operated upon. The passage 40 may also be used for access (e.g., as by sliding a small sensor wire (not shown) through the passage) to monitor pressure or temperature in the area of operation. In the first embodiment, the inner end of the shaft 36 opposite the free end 38 is located in a cavity 44 inside the grip 22 (FIG. 1). The inner end is sealingly connected to one end of a collapsible tube portion 46 by an annular plug 48. The opposite end of the collapsible tube portion 46 is sealing connected to a rigid tube portion 50 which passes out of the cavity 44 and grip 22 through the second end 26 of the grip. The collapsible tube portion 46 and the rigid tube portion 50 together constitute means for conducting fluid between the inner end of the surgical tool 34 and the exterior of the grip 22. A vacuum source or source of irrigating fluid (not shown) may be connected to the end of the rigid tube portion 50 outside the grip 22 for providing irrigation or aspiration through the surgical tool 34. The location of the opening of the passage 40 at the free end 38 of the surgical tool facilitates the application of vacuum pressure to hold tissue. It can be particularly difficult in eye surgery to pick up certain membranes within the eye. It is believed that by application of vacuum pressure at the tip of the tool 34 through the passage 40, the membranes may be more easily grasped by the tool.

The collapsible tube portion 46 is made of silicone, plastic or other suitable material which is sufficiently flexible and resilient to permit the tube portion to be collapsed by application of a sufficient force, and to resume its original shape when that force is removed. The collapse of the tube portion 46 interrupts the flow of fluid through the passage 40 in the surgical tool 34. The tube portion 46 may be selectively collapsed by operation of a plunger 52 mounted in an opening in the grip 22 which extends from the cavity 44 to the exterior of the grip. The plunger 52 is mounted on the grip 22 by a ring 54 of resilient material extending around the plunger in the opening. The outer periphery of the ring 54 is attached to the grip 22 generally around the opening, and the inner periphery of the ring is attached to the plunger 52.

The plunger 52 is sized and shaped to be depressed by a surgeon's finger to move downwardly into the cavity 44 and against the collapsible tube portion 46. Continued downward movement of the plunger 52 pinches shut the collapsible tube portion 46 against a block 56 formed in the cavity 44. As the plunger 52 is pushed down from its FIG. 1 position above the collapsible tube portion 46, the resilient ring 54 is deflected from its relaxed configuration. Thus, when pressure on the plunger 52 is released, the ring 54 pulls the plunger upward away from the collapsible tube portion 46. The resiliency of the collapsible tube portion 46 also facilitates its reopening upon release of pressure on the plunger 52. Although the collapsible tube portion 46 is normally open in the surgical instrument 20 of the first embodiment, it would be possible to bias the plunger 52 to pinch shut the tube portion in the normal position and to provide linkage (not shown) to move the plunger away from the tube portion by operation of the surgeon, and still fall within the scope of this invention.

The illuminated surgical instrument 20 further comprises a plurality of light conducting fibers 60 which extend through the tubular member 28 and have terminal ends 62 located generally at the distal end 30 of the member. The fibers 60 may be made of plastic, quartz, glass, silica or other suitable light conducting material. However, the fibers are preferably made of an inexpensive plastic polymethylmethacrylate) so that the entire instrument 20 can be inexpensively made, and therefore disposable after one use. The fibers 60 exiting the inner end of the tubular member 28 in the grip 22 pass from the cavity 44 into a fiber passage 64 formed in the grip and out the second end 26 of the grip. Near the second end 26 of the grip, the fibers 60 are bundled in a plastic sleeve 66 and extend to a connector (not shown) which can be connected to a light source (not shown). One or more of the fibers 60 may be connected to a laser light source 63 or another energy source (not shown) such as an ultraviolet light source. The laser light source 63 could be activated to, for instance, cauterize a vessel, or ablate certain tissue in the body without the need to remove the instrument 20 and insert a separate cauterizing or ablating instrument (not shown). It is also envisioned that one or more of the fibers 60 could be replaced by a tool (not shown) extending outwardly from the end of the tubular member 28 and capable of manipulating tissue. The terminal ends 62 of the fibers are capable of emitting light conducted from the light source to illuminate the portion of the surgical tool 34 extending outwardly from the distal end 30 of the tubular member 28 and an area of operation generally adjacent to the free end 38 of the surgical tool.

The light fibers 60 are arranged at the open distal end 30 of the tubular member 28 generally around the shaft 36 of the tool. As shown in FIG. 4, the fibers 60 completely surround the shaft 36 in the first embodiment. Thus, light is emitted from all around the shaft 36 toward the free end 38 where the surgical operation is carried out. In this way, the surgical tool 34 is thoroughly illuminated and the formation of shadows cast by the free end 38 of the tool is inhibited. More specifically, although the light emanating from the terminal end 62 of one of the fibers 60 may, depending on the orientation of the tool 34 relative to the area of operation, tend to cast a shadow, light from the other fibers around the shaft 36 will eliminate or substantially abate any such shadow and provide the needed illumination.

The light conductiton fibers 60 are preferably secured to one another in the tubular member 28 as by an epoxy in a formation which extends along a curve around the central axis A of the tubular member 28. The light conducting fibers 60 may or may not be anchored to the tubular member 28. It may be desirable to permit the fibers 60 to be moved relative to the tubular member, in which case the fibers would not be anchored to the tubular member.

Referring now to FIG. 5, a second embodiment of the surgical instrument 220 is shown in which the surgical tool 234 is slidably received in the tubular member 228. Parts of the second embodiment corresponding to the same parts in the first embodiment will be indicated by the same reference numerals, but with the addition of the prefix "2". In the second embodiment, the surgical tool 234 extends substantially continuously from its free end (not shown) to an opposite end 235 outside the second end 226 of the grip 222. The tool 234 (and passage 240 within the tool) widens within the cavity 244 in the grip to permit aspirated solids to more easily pass through of the passage.

The surgical tool 234 is slidably received both by the grip 222 and the tubular member 228 so that it may be moved longitudinally and rotationally relative to the grip, tubular member and light conducting fibers 260 within the tubular member. This capability for adjustment permits the tool 234 and light fibers 260 to be positioned relative to each other for optimum lighting. To hold the surgical tool 234 in place once positioned, a split tube 268 and nut 270 are provided at the second end of the grip to releasably grasp the surgical tool. The surgical tool 234 passes through the split tube 268, which has a longitudinal slot 272 and threads 274 on its exterior. The nut 270 is rotatable on the threads 274 and deforms the split tube 268 inwardly as it is tightened down on the tube and into engagement with the tool 234. The split tube 268 and nut 270 constitute means for releasably fixing the position of the surgical tool 234 in this embodiment.

A third embodiment of the present invention, illustrated in FIGS. 6–8 of the drawings, comprises an illuminatin device 376 capable of being releasably mounted on a surgical tool 334. Parts of the third embodiment corresponding to similar parts in the first embodiment will be indicated by the same reference numeral but with the prefix "3". In this embodiment, the grip 322 and tool 334 are assembled as a unit, but the tubular member 328 and associated light conducting fibers 360 are capable of being disconnected from the tool for sterilization and reuse on the same or different surgical tool. Thus, the fibers 360 are made of quartz or glass. However, the device could also be made to be disposable, in which case the fibers would be formed of an inexpensive plastic. In this embodiment, the surgical tool 334 is a grasping tool having fingers 378 which can be brought together by depressing levers 380 on the grip 322. However, the illuminating device 376 may be used with other surgical tools (e.g., a pick similar to the tool 34 of the first embodiment) and still fall within the scope of the present invention.

The tubular member 328 has a longitudinal slit 382 which extends the its full length. In this embodiment, there is one fewer light conducting member 360 than in the first embodiment, providing an open path from the slit 382 to the central longitudinal axis A of the tubular member 328. The illuminating device 376 is mounted on the surgical tool 334 by pushing the illuminating device onto the tool so that the shaft 336 of the tool passes radially through the slit 382. The shaft 336 engages the two light conducting fibers 360 adjacent to the slit 382 and wedges them apart thereby simultaneously causing the tubular member 328 to flex outwardly such that the transverse dimension of the slit is expanded. Once the shaft 336 is past the two light conducting fibers 360 and lies generally on the central longitudinal axis A of the tubular member 328, the tubular member snaps back to its relaxed position to capture the shaft within the tubular member. The illuminating device 376 can be removed from the shaft 336 by pulling with sufficient force to flex the tubular member 328 and permit passage of the shaft between the two light conducting members 360 adjacent to the slit and out through the slit.

In a fourth embodiment of the invention shown in FIG. 9, the illuminating device 476 further includes at least one door 484 mounted by a hinge 486 on the tubular member 428 adjacent the slit 482. The door 484 may be swung open, as shown in FIG. 9, to expose the slit 482 and permit passage of the shaft 436 of the surgical tool into the tubular member 428. The door 484 is then shut to close the slit 482 (as shown in phantom in FIG. 9). The door 484 carries a light conducting fiber 460' which moves with the door. Thus, when the door 484 is shut, the shaft 436 of the tool is completely surrounded by light fibers 460, 460' as in the first embodiment of this invention. The position of the light fiber 460' when the door 484 is closed is shown in phantom in FIG. 9.

In a fifth embodiment of the invention, the surgical instrument 520 is a cauterizing tool 534 having a suitable grip (not shown). The tubular member 528 constitutes a first tubular electrode which extends from the first end of the grip to the open distal end 530, as shown in FIG. 10. The surgical tool of this embodiment is a second electrode 534 which extends along the central axis A of the tubular first electrode 528. The first and second electrodes (528, 534) are capable of being oppositely charged so as to cause an electrical discharge between them at the distal end 530 of the first electrode for cauterizing a vessel (not shown).

The light conducting fibers 560 surround the second electrode 534 and are disposed between the first and second electrodes to provide electrical insulation between the two. As in the first embodiment, the light conducting fibers have terminal ends 562 located at the distal end 530 of the first electrode 528 (tubular member) and are capable of emitting light conducted from a light source to illuminate the area of operation of the instrument 520.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. An illuminated intraocular surgical instrument, comprising:

a grip having first and second ends;

a tubular member supported by the grip, the tubular member having a central longitudinal axis and an open distal end spaced away from the first end of the grip, the member being sized for insertion through the outer envelope of a living body for surgical operation within the body;

a surgical tool having a shaft extending from within the tubular member outwardly from the distal end of the member, the tool having a free end spaced outwardly from the distal end of the tubular member;

a plurality of light conducting fibers extending through the tubular member and having terminal ends located generally at the distal end of the member, the terminal ends of the fibers being capable of emitting light axially from the open distal end of the tubular member;

the shaft of the tool extending generally along the longitudinal axis of the tubular member as it exits the member through its open distal end, the light fibers being arranged at the open distal end of the member generally around the shaft of the tool within the tubular member, each light fiber engaging the tubular member, the shaft of the tool and an adjacent light fiber in a closely compact relation within the tubular member, thereby to illuminate the portion of the surgical tool located outwardly of the distal end of the member and the area of operation, and to inhibit the casting of shadows by the surgical tool in the area of operation.

2. An illuminated intraocular surgical instrument as set forth in claim 1 wherein the light conducting fibers surround the shaft of the surgical tool at the open distal end of the tubular member, each light fiber contacting an adjacent light fiber to form a substantially continuous light emitting ring around the shaft of the surgical tool.

3. An illuminated intraocular surgical instrument as set forth in claim 1 wherein the free end of the surgical tool outside the tubular member is formed for manipulating tissue within the body.

4. An illuminated intraocular surgical instrument as set forth in claim 3 wherein the surgical tool has a longitudinal passage therein opening at the free end of the tool and at an inner end of the tool opposite the free end.

5. An illuminated intraocular surgical instrument as set forth in claim 4 further comprising means connected to the surgical tool at its inner end within the grip for conducting fluid between the inner end of the tool and the exterior of the grip, said conducting means comprising a collapsible tube portion capable of being selectively collapsed to interrupt the flow of fluid through said conducting means and the surgical tool, the surgical instrument further comprising a plunger mounted on the grip for movement relative to the grip, the plunger being capable of actuation for movement into engagement with the collapsible tube portion inside the grip for collapsing the tube portion.

6. An illuminated intraocular surgical instrument as set forth claim 5 wherein the surgical tool and light conducting fibers are capable of adjustment longitudinally of one another.

7. An illuminated intraocular surgical instrument as set forth in claim 6 wherein the surgical tool is slidably received in the tubular member for movement rotationally and longitudinally of the member.

8. An illuminated intraocular surgical instrument as set forth in claim 7 further comprising means for releasably fixing the position of the surgical tool relative to the tubular member and light conducting fibers.

9. An illuminated intraocular surgical instrument as set forth in claim 1 further comprising a laser light source connected to at least one of the light conducting fibers.

10. An illuminated intraocular surgical instrument as set forth in claim 1 wherein the tubular member and light fibers carried by the tubular member 5 are constructed and arranged for releasable snap on connection to the shaft of the surgical tool.

11. An illuminated intraocular surgical instrument as set forth in claim 10 wherein the tubular member has a longitudinal slit therein through which the shaft of the surgical tool may be passed for mounting the tubular member on the shaft.

12. An illuminated intraocular surgical instrument as set forth in claim 11 wherein the tubular member is constructed to resiliently flex to expand the transverse dimension of the slit.

13. An illuminated intraocular surgical instrument as set forth in claim 12 wherein the tubular member comprises a door hingedly mounted on the member adjacent to the longitudinal slit for swinging motion between a closed position in which the door closes the slit and an open position in which the slit is exposed for passing the shaft of the surgical tool therethrough.

14. An illuminated intraocular surgical instrument as set forth in claim 13 wherein at least one of said light conducting fibers is mounted on the door for motion therewith.

15. An illuminating device for a surgical tool comprising:
a tubular member having a central longitudinal axis and an open distal end, the tubular member having a longitudinal slit therein;
a plurality of light conducting fibers extending through the tubular member and having terminal ends located generally at the distal end of the tubular member, the terminal ends being capable of emitting light to illuminate an area outward of the distal end of the tubular member;
the tubular member and light fibers carried thereby being constructed and arranged for releasable snap on connection to the surgical tool such that the shaft of the tool is received through the slit in the tubular member into the tubular member and between at least two of the light fibers.

16. An illuminating device as set forth in claim 15 wherein the tubular member is constructed to resiliently flex to expand for snapping onto the tool.

17. An illuminating device as set forth in claim 16 wherein the tubular member comprises a door hingedly mounted on the member adjacent to the longitudinal slit for swinging motion between a closed position in which the door closes the slit and an open position in which the slit is exposed for passing a tool therethrough.

18. An illuminating device as set forth in claim 17 wherein one of said light conducting fibers is mounted on the door for motion therewith.

19. An illuminated device as set forth in claim 15 wherein the light conducting fibers are arranged along a curve extending substantially around the central longitudinal axis of the tubular member.

20. An illuminated surgical instrument comprising:
a grip having first and second ends;
a tubular first electrode supported by the grip, the tubular first electrode having a central longitudinal axis and an open distal end spaced away from the first end of the grip, the tubular first electrode being sized for insertion through the outer envelope of a living body for surgical operation within the body;
an elongate second electrode extending through the tubular first electrode generally along its central longitudinal axis, the second electrode being adapted to carry an opposite electrical charge from the tubular first electrode;
a plurality of light conducting fibers extending through the tubular first electrode and having terminal ends located generally at the distal end of the tubular first electrode, the terminal ends of the fibers being capable of emitting light to illuminate an area of operation;
the light conducting fibers being disposed between the tubular first electrode and the second electrode and being constructed for electrically insulating the tubular first electrode from the second electrode, the light conducting fibers surrounding the second electrode generally at the open distal end of the tubular first electrode.

21. A disposable, illuminated intraocular surgical instrument, comprising:

a grip made of plastic and having first and second ends;

a tubular member supported by the grip, the tubular member having a central longitudinal axis and an open distal end spaced away from the first end of the grip, the member being sized for insertion through the outer envelope of a living body for surgical operation within the body;

a surgical tool having a shaft extending from within the tubular member outwardly from the distal end of the member, the tool having a free end spaced outwardly from the distal end of the tubular member;

a plurality of light conducting fibers made of plastic, the fibers extending through the tubular member and having terminal ends located generally at the distal end of the member, the terminal ends of the fibers being capable of emitting light axially from the open distal end of the tubular member;

the shaft of the tool extending generally along the longitudinal axis of the tubular member as it exits the member through its open distal end, the light fibers being arranged at the open distal end of the member generally around the shaft of the tool within the tubular member, each light fiber engaging the tubular member, the shaft of the tool and an adjacent light fiber in a closely compact relation within the tubular member, thereby to illuminate the portion of the surgical tool located outwardly of the distal end of the member and the area of operation, and to inhibit the casting of shadows by the surgical tool in the area of operation.

22. A disposable, illuminated intraocular surgical instrument as set forth in claim 21 wherein:

the light conducting fibers surround the shaft of the surgical tool at the open distal end of the tubular member, each light fiber contacting an adjacent light fiber to form a substantially continuous light emitting ring around the shaft of the surgical tool;

the free end of the surgical tool outside the tubular member being formed for manipulating tissue within the body;

the surgical tool having a longitudinal passage therein opening at the free end of the tool and at an inner end of the tool opposite the free end, the longitudinal passage being adapted for use in aspiration and irrigation through the free end of the tool.

* * * * *